US007322693B2

(12) United States Patent
Abraham

(10) Patent No.: US 7,322,693 B2
(45) Date of Patent: Jan. 29, 2008

(54) FOCUS-ENHANCING BLINDERS

(76) Inventor: Carl J. Abraham, 3 Baker Hill Rd., Great Neck, NY (US) 11023

( * ) Notice: Subject to any disclaimer, the term of this patent is extended or adjusted under 35 U.S.C. 154(b) by 0 days.

(21) Appl. No.: 11/273,672

(22) Filed: Nov. 14, 2005

(65) Prior Publication Data
US 2007/0109492 A1 May 17, 2007

(51) Int. Cl.
G02B 1/00 (2006.01)
(52) U.S. Cl. .................. 351/158; 351/44; 351/155; 2/15
(58) Field of Classification Search ............... 351/41, 351/44, 47, 48, 57, 58, 155, 158; 2/10, 15, 2/452
See application file for complete search history.

(56) References Cited

U.S. PATENT DOCUMENTS

| 3,226,729 | A | * | 1/1966 | Faucci ............................. 2/12 |
| D204,023 | S | * | 3/1966 | Potts ........................ D29/109 |
| 4,969,649 | A | * | 11/1990 | Lugiewicz .................. 473/210 |
| 5,884,334 | A | * | 3/1999 | Collette et al. .............. 2/195.1 |
| 6,079,052 | A | * | 6/2000 | Veridiano ..................... 2/172 |
| 2004/0214147 | A1 | * | 10/2004 | Robinson ................... 434/247 |

* cited by examiner

Primary Examiner—Huy K Mai

(57) ABSTRACT

Focus enhancing blinders for usage in sporting activities and other activities that require visual focus and concentration. More particularly, the invention is a perspiration-absorbing headband worn by players of tennis and other sports where hand-eye coordination is critical. In one mode, the headband includes a slot to hold and guide blinders that extend to the areas on the outside of each eye, functioning to block off a previously-determined degree of peripheral vision. This assists a player in the difficult task of keeping his or her visual focus straight ahead and directly on a ball, thus enhancing the user's performance. This also keeps one reading or studying focused on the task at hand. In the preferred mode, the blinders are of a length of one to four inches and are held in place through the usage of Velcro on the inside of the blinders and outside of the headband. In the preferred mode, Velcro is also placed along the ear on both sides past the open slot to hold the blinders. Importantly, the blinders can move out from the slot to cover the peripheral vision as required. The user may utilize both blinders, one blinder, or neither; as the player improves on his or her focus, the blinders can be moved back toward the ear to a point where they are no longer required.

15 Claims, 3 Drawing Sheets

FOCUS-ENHANCING BLINDERS

BACKGROUND OF THE INVENTION

1. Field of the Invention

The present invention comprises focus enhancing blinders for usage in sporting activities and other activities that require visual focus and concentration. More particularly, the invention is a perspiration-absorbing headband worn by players of tennis and other sports where hand-eye coordination is critical.

In one mode, the headband includes a slot to hold and guide blinders that extend to the areas on the outside of each eye, functioning to block off a previously-determined degree of peripheral vision. This assists the user in the difficult task of keeping his or her visual focus straight ahead and directly on the ball, thus enhancing the user's performance.

In addition, the blinders are of a length of one to four inches and can be held in place through the usage of Velcro on the inside of the blinders and outside of the headband. In the preferred mode, Velcro is also placed along the ear on both sides past the open slot to hold the blinders. Importantly, the blinders can move out from the slot to cover the peripheral vision as required. The user may utilize both blinders, one blinder, or neither; as the player improves on his or her focus, the blinders can be moved back toward the ear to a point where they are no longer required.

2. Description of the Prior Art

Numerous innovations for focus-enhancing devices have been provided in the prior art that are described as follows. Even though these innovations may be suitable for the specific individual purposes to which they address, they differ from the present invention as hereinafter contrasted. The following is a summary of those prior art patents most relevant to the invention at hand, as well as a description outlining the differences between the features of the present invention and those of the prior art.

1. U.S. Pat. No. 5,675,398, invented by Moore, entitled "Sports Training Eyeglasses having Adjustable Lenses and Method For Training Therewith"

A pair of eyeglasses is provided for sports training, and more specifically for training the player to keep the player's eyes on an approaching ball for batting or for swinging a racket. The pair of glasses, have a position adjustable pair of lenses each having an opaque peripheral region and a transparent central region. Initial adjustment of the lenses is achieved utilizing a removable cover element overlaying the transparent central region wherein the cover element has a viewing aperture. A method is provided wherein the player wears a pair of the glasses, adjusts the positions of the lenses to correspond to the positions of the pupillary disks of the player until the player can view a single focal element through each aperture, removing the cover elements from the lenses, and batting at a moving ball while wearing the eyeglasses.

2. U.S. Pat. No. 6,390,619, invented by Gin, entitled "Vision Directing Goggle"

A vision directing goggle for directing a batter's vision during batting practice. The vision directing goggle includes a housing for directing the vision of a user. The housing is generally rectangular and has an open top side and an open bottom side. The housing has a first pair of opposing walls and a second pair of opposing walls. An elastomeric strap binds the housing to a user's head. A coupling means couples the strap member to the housing. The coupling means is affixed to an outside surface of each of the second opposing walls.

3. U.S. Pat. No. 6,513,928, invented by Moore, entitled "Sports Training Eyeglasses"

A pair of sports training eyeglasses is provided for training a user to keep his/her eye on a ball while hitting either a stationary ball, e.g. in golf or hockey, or a moving ball, e.g., in baseball and softball. The pair of sports training eyeglasses have a pair of lenses, each lens having an opaque peripheral region and a viewing aperture, and a frame having an elongated bridge bar having opposite ends, a pair of opposing temporal side members extending from respective ends of the elongated bridge bar, a means for adjusting the position of each temporal side member in relation to the elongated bridge bar, a movably nose piece, a means for removably attaching each lens to the elongated bridge bar, wherein the position of each lens is adjustable in relation to the nose piece, and a means for locking the position of each lens on the elongated bridge bar. A first set of lenses is provided having an oval shaped viewing aperture and is used in training a user to hit a moving ball. A second set of lenses is provided having a viewing aperture being an elongated slit that is rotatable between a vertical orientation for fitting the lenses on a user and a horizontal orientation for training the user to hit a stationary ball. A method is also provided wherein a user adjusts the pair of eyeglasses to a comfortable fit, wears the pair of eyeglasses, adjusts the position of the lenses, locks the position of the lenses, and trains in hitting either a moving ball or a stationary ball depending on whether the first set of lenses or the second set of lenses are installed, respectively.

4. U.S. Pat. No. 6,826,784, invented by Patire, entitled "Controlled Sight Device"

An eye shield assembly useful in training students in non-deadly force, firearms and martial arts has an opaque first eye shield which is coupled to an apertured second eye shield by connecting together adjustable straps on both eye shields. One eye shield covers the eyes while the other eye shield forms a portion of the head strap. The opaque first eye shield simulates substantial or complete blindness while the apertured second eye shield simulates tunnel vision, both conditions being possible during an encounter with an adversary. By utilizing the eye shield assembly, the trainee becomes acclimated to sight impairment and learns to employ the skills obtained by his or her training in situations where there is sight impairment.

5. U.S. Design Pat. D502,493, invented by Moore, entitled "Sports Training Eyeglasses"

An ornamental design for a sports training eyeglasses.

6. U.S. Pat. No. 4,531,743 invented by Lott, entitled "Golfer's Aid"

A golfer's aid is provided in the form of a translucent sheet having two transparent crosses thereon wherein the center of the crosses corresponds with the separation of a user's eyes, and a pair of vertical and horizontal slots, respectively, above and at the outer sides of said crosses, said sheet being pivotally supported by extension arms well in front of the user's eyes.

7. U.S. Pat. No. 5,050,982 invented by Meissner, entitled "Method And Apparatus For Improving Visual Acuity"

A method and apparatus for improving visual acuity during sports activities includes increasing the strength of the image on the brain half corresponding to the weaker eye by substantially occluding ambient light to the dominant eye of the person for a period of approximately one to two weeks for at least one hour per day; forcing both brain halves to operate at substantially equal visual levels in coordination with each other by wearing eyeglasses having inner opaque sections adjacent the nose bridge so as to limit overlapping vision of the two eyes to a small overlapping area, the inner opaque areas being inwardly and downwardly inclined at an angle of approximately 20 with respect to a nasal axis extending through the nose of the person; and forcing both brain halves to operate independently of each other at substantially equal visual levels by increasing the areas of the opaque sections so as to eliminate the overlapping area, which forces each brain half to process the visual information supplied to it independently of the other brain half, such that the eyes of the person can operate independently and in synchronism, with the same angle of approximately 20 being maintained.

8. U.S. Pat. No. 4,392,650 invented by Hilton, entitled "Tennis Training Aid"

A training aid primarily adapted to teach a tennis player proper form includes a hood, a headband, and an indicator for indicating when the user's head is tilted downwardly. The hood restricts peripheral vision and requires concentration on the ball. The indicator and hood may move relative to each other so that the indicator moves into the user's field of vision upon tilting of the hood.

9. U.S. Pat. No. 4,605,226 invented by Morrissey, entitled "Head Guide and Batting Helmet"

A sports training device which includes an opaque shield releasably mounted on a protective helmet on the side opposite the source of a projectile travelling toward the user, in the case of baseball, or on the side facing the direction of intended flight of the ball to be struck whereby movement of the user's head out of the desired position results in the shielding of the eyes of the user from the projectile.

10. U.S. Pat. No. 4,969,649 invented by Lugiewicz entitled "Performance Enhancement Apparatus"

A performance enhancement aid for sports activities and the like in which it is necessary to keep the eyes focused on a target. The aid may be an assembly mounted on the user's eyeglasses or the eye direction panels may be permanently fixed to a frame which is worn on the head in a manner similar to eyeglasses. A pair of opaque panels are supported on opposite sides of the user's eyes. Each panel has a forward portion which extends obliquely inwardly toward and aligned with the optical axis line of the adjacent eye when the user's eyes are focused on a target. Each oblique extension defines a desired sight line. The two defined sight lines converge at a line bisecting the angle formed by the optical axis lines of the user's eyes, thereby directing the eyes to the target.

SUMMARY OF THE INVENTION

The present invention comprises focus enhancing blinders for usage in sporting activities and other activities in which visual focus and concentration are important. For example, the invention is a perspiration-absorbing headband that can be worn by players of tennis and other sports where hand-eye coordination is critical to performance.

In one mode, the headband includes a slot to hold and guide blinders that extend to the areas on the outside of each eye, functioning to block off a previously-determined degree of peripheral vision. This assists the user in the difficult task of keeping his or her visual focus straight ahead and directly on the ball, thus enhancing the user's performance.

In addition, the blinders are of a length of one to four inches and may be held in place through the usage of Velcro on the inside of the blinders and outside of the headband. In the preferred mode, Velcro is also placed along the ear on both sides past the open slot to hold the blinders. Importantly, the blinders can move out from the slot to cover the peripheral vision as required. The user may utilize both blinders, one blinder, or neither; as the player improves on his or her focus, the blinders can be moved back toward the ear to a point where they are no longer required.

In light of the foregoing, it is an object of the present invention to provide a device to enhance players' performance in a variety of sporting activities, including racquet sports and golf.

It is a further object of the invention to provide an apparatus that specifically improves a player's hand-eye coordination.

It is also an object of the present invention to provide a focus-enhancing device that can be used for non-sporting activities where concentration is important, including reading, studying, and performing medical procedures.

It is a further object of the present invention to provide a device that is relatively inexpensive to manufacture and produce.

In addition, it is an object of the present invention to provide vision enhancing blinders that may be adjusted by the user according to the user's development.

Finally, it is an object of the present invention to provide vision enhancing blinders that may be conveniently attached to a perspiration absorbing sweatband through the usage of VELCRO or hook and loop fasteners.

The novel features which are considered characteristic for the invention are set forth in the claims. The invention itself, both as to its construction and its method of operation, together with additional objects and advantages thereof, will be best understood from the following description of the embodiments when read and understood in connection with accompanying drawings.

DETAILED DESCRIPTION

Figure 1:
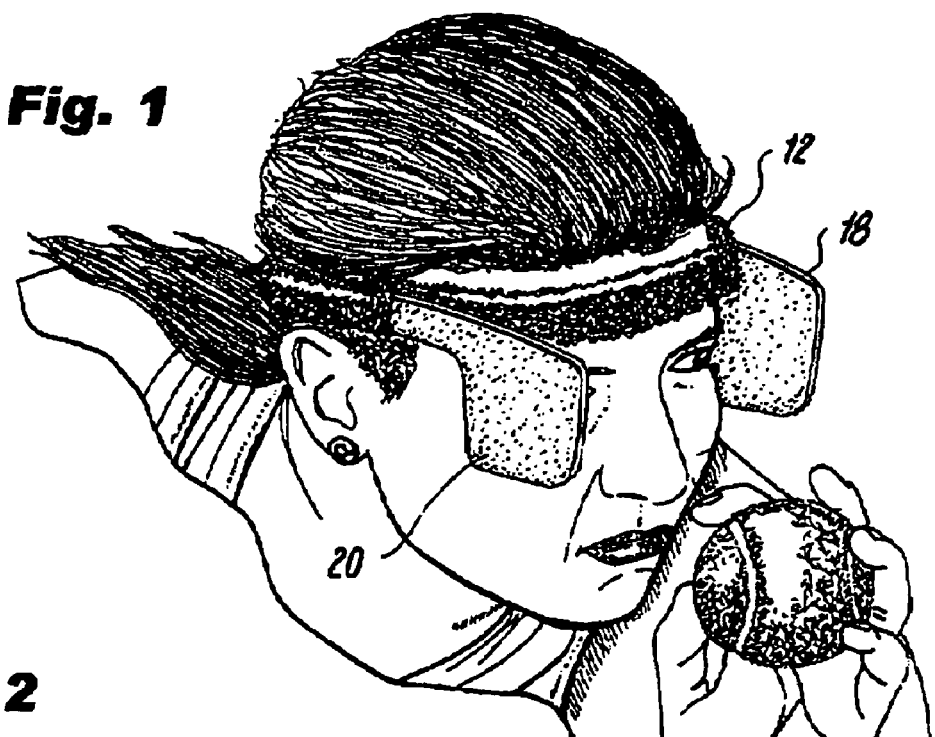
FIG. 1 is a perspective view of the principal embodiment of the present invention in use.
Figure 2:
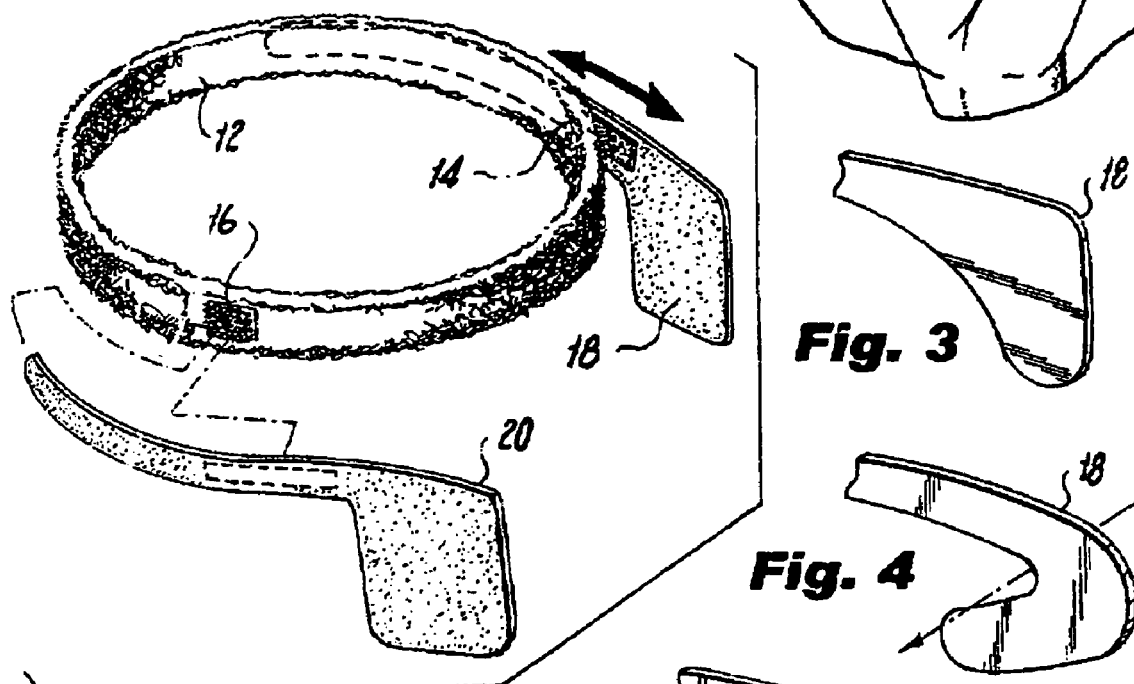
FIG. 2 is a front three-quarter perspective view of the principal embodiment of the present invention only.
Figure 3:
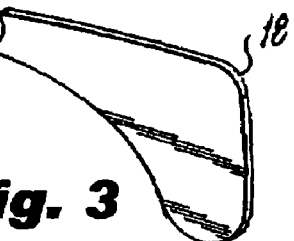
FIG. 3 is a side perspective view of a blinder member of the present invention only.
Figure 4:
FIG. 4 is a side perspective view of a blinder member of the present invention only, including cut-away showing sightline and blockage thereof.
Figure 6:
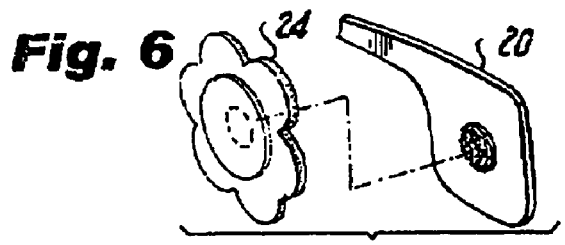
FIG. 6 is a side perspective view of a blinder member of the present invention, including optional accessories.
Figure 5:
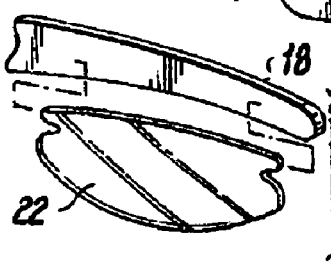
FIG. 5 is a side perspective view of a blinder member of the present invention, including optional and removable tinted lens.
Figure 7:
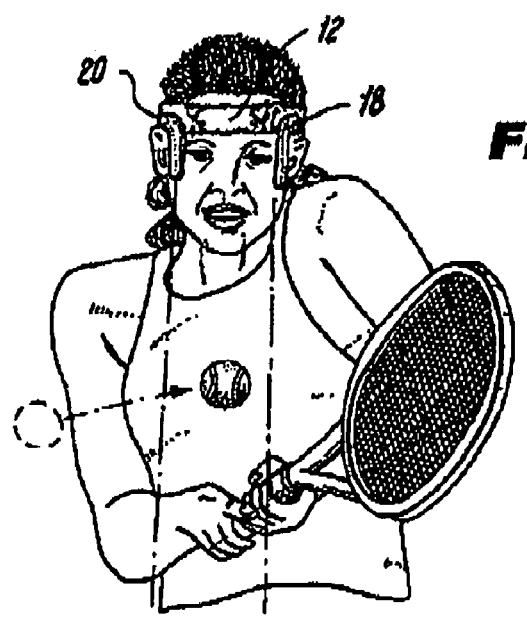
FIG. 7 is a perspective view of the principal embodiment of the present invention in use for tennis and other racquet sports.
Figure 8:
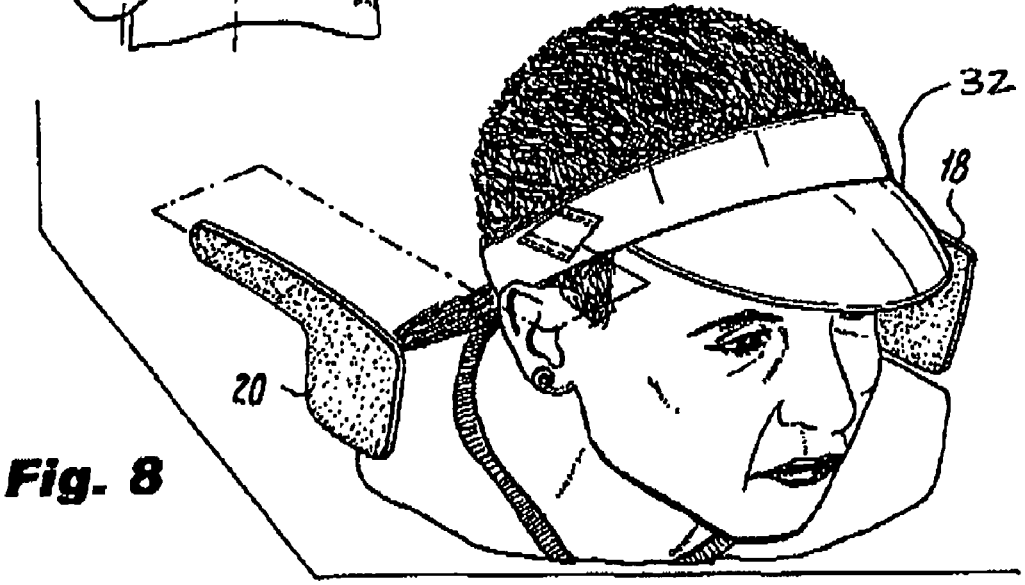
FIG. 8 is a perspective view of the principal embodiment of the present invention used in conjunction with a previously existing visor.
Figure 9:
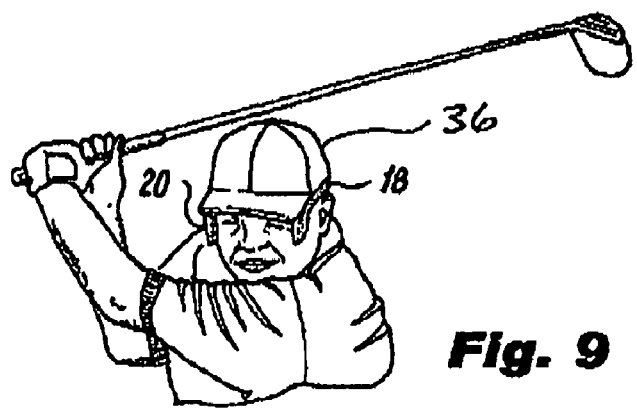
FIG. 9 is a perspective view of the principal embodiment of the present invention in use for golf.
Figure 11:
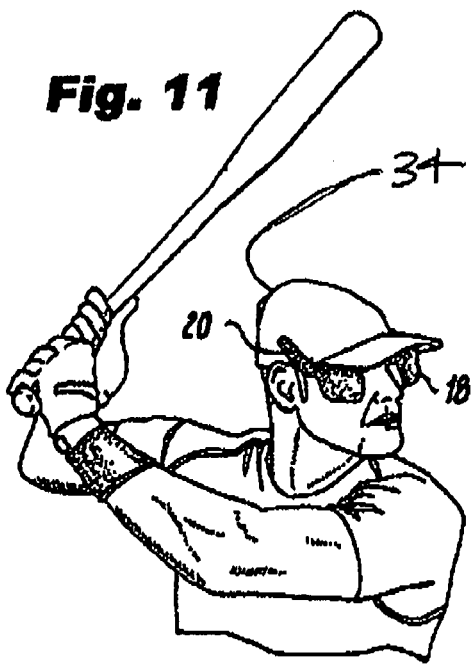
FIG. 11 is a perspective view of the principal embodiment of the present invention in use for baseball on a batter.
Figure 10:
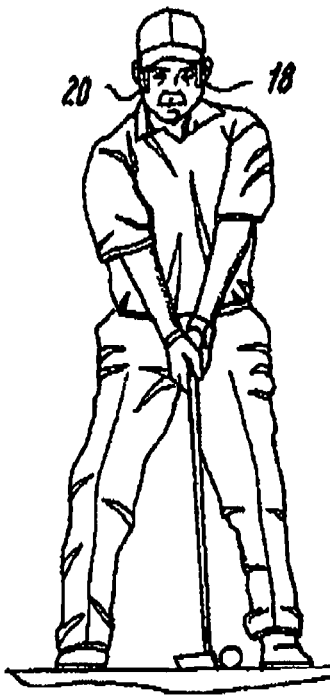
FIG. 10 is a perspective view of the principal embodiment of the present invention in use for golf on a player in the act of driving a golf ball.
Figure 12:
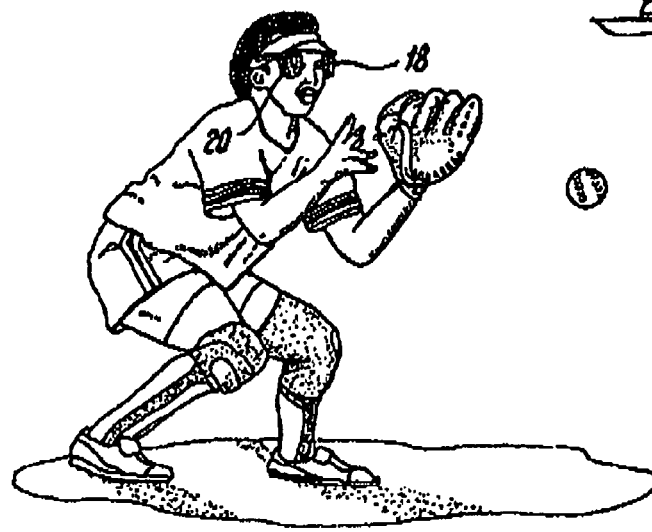
FIG. 12 is a perspective view of the principal embodiment of the present invention in use for baseball on a catcher.
Figure 13:
FIG. 13 is a perspective view of the principal embodiment of the present invention in use for reading, studying, or other academic activities.

In all embodiments, the focus-enhancing blinder apparatus comprises a generally annular headband (12) which absorbs perspiration in the traditional manner. The headband of the present invention comprises a left blinder member (18) which is affixed to a left side of the headband, and is preferably removable.

The left blinder member extends outwardly to a previously-determined area of an outside of a user's left eye. This functions to block off a previously-determined degree of the user's peripheral vision for the left eye.

Likewise, the headband further comprises a right blinder member (20) which is affixed to a right side of the headband, again preferably removably affixed. Similar to the left blinder member, the right blinder member extends outwardly to a previously-determined area of an outside of the user's right eye. This functions to block off a previously-determined degree of the user's peripheral vision for the right eye as well.

The left blinder and right blinder may each be curved to simulate the shape of the user's head. Alternatively, the left blinder and right blinder may each be straight in configuration, if desired for the type of activity in question. In either instance, the left blinder and right blinder may each be of a length in the range of one to four inches. Moreover, for versatility in manufacture, the blinders may be constructed of any of a variety of materials, such as plastic, nylon, cardboard, paper, and foam.

Importantly, the apparatus of the present invention functions to assist the user in keeping the user's visual focus straight ahead, rather than wandering off to the sides peripherally. When used in a sporting activity, this mitigates the natural tendency to look to the sides and thus facilitates keeping the user's visual focus directly on the ball or other item used in the sport. The result is a significant improvement in the hand-eye coordination of the user. Because this enhances the user's performance in the sporting activity, it provides an excellent training tool, uniquely teaching the player the level of focus needed to excel in the activity in question.

Regarding the construction of the device, in a first mode, the headband comprises a left slot (14) in which a first end of the left blinder is inserted. The left slot functions to hold and guide the left blinder, such that the left blinder can move outwardly from the left slot to block the user's peripheral vision as desired.

Likewise in the first mode, the headband comprises a right slot (16) in which a first end of the right blinder is inserted. The right slot functions to hold and guide the right blinder, such that the right blinder can move outwardly from the right slot to block the user's peripheral vision as desired.

In a second mode of production, the left blinder and right blinder are removably affixed to the headband through usage of hook and loop fasteners. In such instance, hook and loop fasteners may be located on an interior surface of the left blinder and right blinder, with corresponding fasteners upon the exterior surface of the headband. Moreover, hook and loop fasteners may also be placed along the ear on both sides, past the open slot to hold the left blinder and right blinder.

In either embodiment, the degree to which the blinders extend outwardly from the headband is adjustable. Specifically, the blinders can be moved back toward the user's ears to a point where the blinders are no longer required as the user's focus improves.

Regarding additional features, the device may comprise indicia thereon. Such may be in the form of decorative items, colors or designs, or may be functional in nature. For the purposes of example only, the device may include a series of marks to indicate the degree to which the blinders are extended outwardly from the headband. This will allow the user to set the extension length to a specific desired degree, and will also allow the user to track his or her progress in the activity at hand.

In addition, the device may further comprise a removable tinted lens (22) for usage in conjunction with outdoor activities. The device may further comprise other removable accessories (24) which are decorative in nature or which are intended to be worn by children to make the wearing of the device more desirable.

It is important to note that the device of the present invention may be worn by a user in conjunction with an item selected from the group consisting of a visor, helmet, and hat. In addition to assisting in keeping the headband in place, the ability to wear the headband with another item renders it suitable for usage in a host of sporting activities. For the purposes of example only, the device may be utilized for activities in which visual focus is important to performance, such as tennis, racquetball, squash, handball, paddleball, badminton, golf, and baseball.

Versions of the blinder apparatus for usage in sporting activities may comprise a generally annular headband which comprises a left blinder member affixed to a left side of the headband, the left blinder member extending outwardly to a previously-determined area of an outside of a user's left eye, functioning to block off a previously-determined degree of the user's peripheral vision, the headband further comprising a right blinder member affixed to a right side of the headband, the right blinder member extending outwardly to a previously-determined area of an outside of the user's right eye, functioning to block off a previously-determined degree of the user's peripheral vision, with versions of the apparatus functioning to assist the user in keeping the user's visual focus straight ahead and directly on an item used in the sporting activity, improving hand-eye coordination of the user, and enhancing the user's performance in the sporting activity. The headband may also comprise a left slot in which a first end of the left blinder is inserted, the left slot functioning to hold and guide the left blinder, such that the left blinder can move outwardly from the left slot to block the user's peripheral vision as desired and further comprises a right slot in which a first end of the right blinder is inserted, the right slot functioning to hold and guide the right blinder, such that the right blinder can move outwardly from the right slot to block the user's peripheral vision as desired. Versions may also include the left blinder and right blinder affixed to the headband through usage of hook and loop fastener. Alternate embodiments utilize hook and loop fasteners are located on an interior surface of the left blinder and right blinder and exterior surface of the headband. Other versions use hook and loop fasteners placed along the car on both sides of the headband past the open slot to hold the left blinder and right blinder. Versions of the device may be worn by a user in conjunction with an item selected from the group consisting of a visor 32, helmet 34, and hat 36. The left blinder and right blinder may be each of a length in the range of one to four inches. Alternate versions of the device are utilized for activities selected from the group consisting of tennis, racquetball, squash, handball, paddleball, badminton, golf, and baseball. Versions of the focus-enhancing blinders may include a degree to which the blinders extend from the headband is adjustable such that the blinders can be moved back toward an ear of a user to a point where they are no longer required as the user improves upon the user's focus. Versions of the device may comprise indicia and previously determined colors and designs and further comprises a tinted lens for usage in conjunction with outdoor activities and further comprises decorative accessories. Other versions may include the left blinder and right blinder each curved to simulate the shape of the user's head or the left blinder and right blinder are each straight. In another version the headband absorbs perspiration. Versions of the device may be used in connection with reading, studying and academic activities and used by members of the medical community in connection with performing medical procedures.

In an alternate mode of usage, the device is used in connection with non-sporting activities in which focus is equally important, such as reading, studying or other academic activities. Usage of the focus-enhancing blinders in this context can be expected to increase academic performance. Moreover, should the student absorb the study material more quickly due to the high level of concentration afforded by the blinders, the total number of hours spent in the act of homework or studying will be reduced, providing an incentive to utilize the focus-enhancing blinders.

The device may also be effectively used by members of the medical community, such as while performing medical procedures. In this context, the user's concentration will again be enhanced due to the blocking of any external visual distractions.

With regards to all descriptions and graphics, while the invention has been illustrated and described as embodied, it is not intended to be limited to the details shown, since it will be understood that various omissions, modifications, substitutions and changes in the forms and details of the device illustrated and in its operation can be made by those skilled in the art without departing in any way from the spirit of the invention.

Without further analysis, the foregoing will so fully reveal the gist of the present invention that others can readily adapt it for various applications without omitting features that, from the standpoint of prior art, constitute essential characteristics of the generic or specific aspects of this invention. What is claimed as new and desired to be protected by Letters Patent is set forth in the appended claims.

What is claimed is:

1. A focus-enhancing blinder apparatus for usage in sporting activities comprising:
    a substantially annular headband which comprises a left blinder member adjustably affixed to a left side of the headband, further comprising;
    the left blinder member further comprising a means for extending outwardly to a predetermined configuration of a user's left eye,
    the headband further comprising a right blinder member adjustably affixed to a right side of the headband,
    the right blinder member further comprising a means for extending outwardly to a predetermined configuration of the user's right eye
    further comprising a left slot in which a first end of the left blinder member is inserted, such that the left blinder member can move outwardly from the left slot to block the user's peripheral vision as desired, further comprising
    a right slot in which a first end of the right blinder member is inserted, such that the right blinder member can move outwardly from the right slot to block the user's peripheral vision as desired.

2. The focus-enhancing blinders apparatus as described in claim 1, wherein the left blinder member and right blinder member are affixed to the headband through usage of hook and loop fasteners.

3. The focus-enhancing blinders apparatus as described in claim 1, wherein hook and loop fasteners are located on an interior surface of the left blinder member and right blinder member and exterior surface of the headband.

4. The focus-enhancing blinders apparatus as described in claim 1, wherein hook and loop fasteners are also placed along a user's ear on a left side of the apparatus and a right side of the apparatus past an open slot to hold the left blinder member and right blinder member.

5. The focus-enhancing blinders apparatus as described in claim 1, wherein the apparatus is worn by a user beneath an item selected from the group consisting of a visor, helmet, and hat, alone or in combination.

6. The focus-enhancing blinders apparatus as described in claim 1, wherein the left blinder member and right blinder member are each of a length in the range of one to four inches.

7. The focus-enhancing blinders apparatus as described in claim 1, wherein the apparatus is utilized for activities selected from the group consisting of tennis, racquetball, squash, handball, paddleball, badminton, golf, and baseball, alone or in combination.

8. The focus-enhancing blinders apparatus as described in claim 1, wherein the apparatus comprises indicia thereon.

9. The focus-enhancing blinders apparatus as described in claim 1, wherein the apparatus bears colors and designs in a predetermined configuration.

10. The focus-enhancing blinders apparatus as described in claim 1, wherein the apparatus further comprises a tinted lens.

11. The focus-enhancing blinders apparatus as described in claim 1, wherein the apparatus further comprises decorative accessories.

12. The focus-enhancing blinders apparatus as described in claim 1, wherein the left blinder member and right blinder member are each curved to simulate the shape of the user's head.

13. The focus-enhancing blinders apparatus as described in claim 1, wherein the left blinder member and right blinder member are each straight.

14. The focus-enhancing blinders apparatus as described in claim 1, wherein the left blinder member and right blinder member are each constructed of a material selected from the group consisting of plastic, nylon, cardboard, paper, and foam, alone or in combination.

15. The focus-enhancing blinders apparatus as described in claim 1, wherein the apparatus absorbs perspiration.

* * * * *